United States Patent
Rosario-Melendez et al.

(10) Patent No.: US 10,688,034 B2
(45) Date of Patent: *Jun. 23, 2020

(54) LONG-WEARING, TRANSFER-RESISTANT COSMETIC COMPOSITION HAVING IMPROVED TACKINESS

(71) Applicant: L'ORÉAL, Paris (FR)

(72) Inventors: Roselin Rosario-Melendez, Piscataway, NJ (US); Rita Jaky El-Khouri, Morristown, NJ (US); Gisela Perruna, Rahway, NJ (US); Ann Marie Rohmeyer, Englishtown, NJ (US); Susan Ashley Desteno, Old Bridge, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/223,746

(22) Filed: Jul. 29, 2016

(65) Prior Publication Data
US 2018/0028432 A1      Feb. 1, 2018

(51) Int. Cl.
| | | |
|---|---|---|
| *A61K 8/891* | (2006.01) | |
| *A61Q 1/04* | (2006.01) | |
| *A61K 8/898* | (2006.01) | |
| *A61K 8/58* | (2006.01) | |
| *A61K 8/81* | (2006.01) | |
| *A61Q 1/06* | (2006.01) | |
| *A61C 1/04* | (2006.01) | |
| *A61C 1/06* | (2006.01) | |

(52) U.S. Cl.
CPC ............... *A61K 8/891* (2013.01); *A61C 1/04* (2013.01); *A61C 1/06* (2013.01); *A61K 8/585* (2013.01); *A61K 8/81* (2013.01); *A61K 8/898* (2013.01); *A61K 2800/31* (2013.01); *A61K 2800/43* (2013.01); *A61K 2800/594* (2013.01)

(58) Field of Classification Search
None
See application file for complete search history.

(56) References Cited

U.S. PATENT DOCUMENTS

| | | |
|---|---|---|
| 5,505,937 A | 4/1996 | Castrogiovanni et al. |
| 5,911,974 A | 6/1999 | Brieva et al. |
| 6,019,962 A | 2/2000 | Rabe et al. |
| 6,027,738 A | 2/2000 | Stepniewski et al. |
| 6,074,654 A | 6/2000 | Drechsler et al. |
| 6,340,466 B1 | 1/2002 | Drechsler et al. |
| 6,387,405 B1 | 5/2002 | Shah et al. |
| 6,555,097 B1 | 4/2003 | Rabe et al. |
| 8,945,525 B2 | 2/2015 | Bradshaw et al. |
| 2003/0049212 A1* | 3/2003 | Robinson ................. A61K 8/06 424/59 |
| 2007/0053859 A1 | 3/2007 | Bui et al. |
| 2010/0297050 A1 | 11/2010 | Bui et al. |
| 2012/0171137 A1* | 7/2012 | Bradsaw ................... A61K 8/31 424/64 |
| 2012/0171138 A1 | 7/2012 | Bradshaw et al. |

FOREIGN PATENT DOCUMENTS

WO    WO 2016/046355    3/2016

OTHER PUBLICATIONS

"What's that stiff?", Lipstick, Jul. 12, 1999, vol. 77, No. 28. (Year: 1999).*
U.S. Appl. No. 15/420,888, filed Jan. 31, 2017, Rita Jaky El-Khouri, et al.
U.S. Appl. No. 15/223,951, filed Jul. 29, 2016, Roselin Rosario-Melendez.
International Search Report and Written Opinion dated Sep. 29, 2017 in PCT/US2017/043719.

\* cited by examiner

*Primary Examiner* — Isis A Ghali
(74) *Attorney, Agent, or Firm* — Polsinelli PC

(57) ABSTRACT

The present invention relates to a cosmetic composition comprising at least one silicone elastomer and at least one non-volatile oil at ratio from about 1:0.2 to about 1:10, at least one silicone resin, at least one volatile solvent and at least one polyorganosiloxane copolymer. The composition of the present invention may optionally contain wax, fillers and/or pigments. The invention also relates to a method for making up and enhancing the appearance of a keratinous substrate, in particular lips, by applying the incentive composition to the keratinous substrate.

14 Claims, No Drawings

LONG-WEARING, TRANSFER-RESISTANT COSMETIC COMPOSITION HAVING IMPROVED TACKINESS

FIELD OF THE INVENTION

The present invention relates to a cosmetic composition and method for making up and/or enhancing the appearance of a keratinous substrate, comprising at least one silicone elastomer, at least one non-volatile oil, at least one silicone resin, at least one volatile solvent and at least one polyorganosiloxane copolymer. The composition of the present invention may optionally contain waxes, fillers and/or pigments.

BACKGROUND OF THE INVENTION

Cosmetic compositions used to make up or enhance the appearance of a user's skin are often required to be able to impart various properties such as long wear, transfer resistance and comfort. However, the formulation of cosmetic products that can deliver these properties at the same time can pose some challenges. For example, cosmetic compositions using traditional ingredients known to impart long wear, such as silicone resins, are very drying. In addition, they cause discomfort and flaking during the use. In order to overcome these problems, oils, such as silicone oils are generally employed. While the utilization of silicone oils in cosmetics is popular, one drawback associated with their use is that they tend to shine and are tacky, which are not always desired effects for the finished products.

Therefore, it is an object of the present invention to provide a composition and method for making up skin in a manner which delivers transfer resistance and long wear properties, as well as superior comfort, non-tacky feel and nonglossy (matte) appearance.

It has been surprisingly discovered that the combination of silicone crosspolymer (elastomer) and silicone oil (fluid) having viscosity greater than 100 cSt at specific ratios, in addition to silicone resins, polyorganosiloxane copolymer and volatile solvent, provides the compositions characterized by non-tacky feel and superior comfort, transfer resistance, long wear and minimal or absence of flaking when applied onto a keratinous substrate. The formulations of the present inventions are also matte.

BRIEF SUMMARY OF THE INVENTION

According to one embodiment of the present invention, there is provided an anhydrous composition which is long wearing and transfer resistant, while at the same time provides superior comfort, non-tacky feel and looks matte, containing:
 (a) from about 1% to about 30% by weight of at least one silicone elastomer;
 (b) from about 2% to about 30% by weight of at least one non-volatile oil;
 (c) from about 2% to about 35% by weight of polyorganosiloxane copolymer;
 (d) from about 5% to about 30% by weight of at least one silicone resin;
 (e) from about 5% or about 50% of at least one volatile;
 (f) optionally at least one wax;
 (g) optionally at least one colorant; and
 (h) optionally at least one filler;
 wherein the ratio of the silicone elastomer (a) to the at least one non-volatile oil (b) is higher or equals to from about 1:0.02, is from about 1:1 to about 1:6 and is lower or equals from about 1:10, by weight, the weights being relative to the total weight of the composition. All numerical values are weight percent solids (actives).

According to a preferred embodiment, the composition further contains at least one colorant, at least one wax, at least one filler and at least one additive.

As per this invention, the inventive compositions are related but not limited to liquid compositions, such as lipsticks, liners, foundations, mascaras, eyeshadows, skin care compositions, sunscreens, skin repellants, deodorants, nail composition.

Another embodiment of this invention pertains to the composition being free or substantially free or devoid of non-volatile solvents having at least one or more phenyl groups. These solvents are for example described in U.S. Pat. No. 8,945,525, the entire content of which is hereby incorporated by the reference.

In another embodiment, the invention is a method of making up skin involving applying onto the skin the above disclosed compositions, as well as a method of making the inventive composition.

As per another embodiment, this invention relates to a system of cosmetic compositions comprising the color coat composition as previously described and a top coat composition.

According to the invention, the term "anhydrous" refers to a composition not containing any water, that is to say a composition in which the water that may be present comes only from the water of crystallization or of adsorption of the starting materials. In any case, an anhydrous composition contains less than 5% by weight of water, preferably less than 1% by weight, and better still less than 0.5% by weight of water, relative to the total weight of the composition.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number (e.g. "about 10%" means 9%-11% and "about 2%" means 1.8%-2.2%).

"Film former" or "film forming agent" or "film forming polymer" or "film forming resin" as used herein mean a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions. For lip compositions, "long wear" typically means the composition remains on the lips at least about 4 hours up to about 24 hours, and retains rich color even after eating.

"Liquid" or "liquid cosmetic" or "liquid lipstick" or "liquid composition" means a composition having a fixed volume, flows to cover the bottom and assumes the shape of the portion of the container it fills and is slightly compressible (as disclosed in *General chemistry*, Fourth Edition 2005, p. 434

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion and the one far along described.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphategroups, siloxane groups, and polysiloxane groups. The substituent(s) may be further substituted.

"Comprising" it is meant that other steps and/or ingredients which do not affect the end result may be added. The products, compositions, methods and processes of the present invention can include all the essential elements and limitations of the invention described herein as well as any of the additional or optional ingredients, components, steps, or limitations described herein.

"Free" or "substantially free" or "devoid of" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention, Thus, for example, "free of phenylated solvents" means that non-volatile solvents are preferably omitted (that is 0% by weight), but can be present in the composition at an amount of less than about 0.25% by weight, typically less than about 0.1% by weight, typically less than about 0.05% by weight, based on the total weight of the composition as a whole.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

As used herein a range of ratios is meant to include every specific ratio within, and combination of subranges between the given ranges.

The compositions and methods of the present invention can comprise, consist of, or consist essentially of the essential elements and limitations of the invention described herein, as well as any additional or optional ingredients, components, or limitations described herein or otherwise useful.

Siloxysilicate Resins

The cosmetic compositions of the present invention comprise at least one silicone resin such as described for example, in U.S. Pat. Nos. 5,505,937, 5,911,974, 5,965,112, 5,985,298, 6,074,654, 6,780,422, 6,908,621, the disclosures of which are hereby incorporated by references.

According to this invention, the cosmetic compositions may contain siloxysilicate resins. One non-limiting example of a siloxysilicate in accordance with the present invention is trimethylsiloxysilicate, which may be represented by the following formula:

wherein x and y may, for example, range from 50 to 80. Such siloxysilicates are commercially available from General Electric, Dow Corning, Wacker, Milliken, Siltech, Grant industries, Momentive and Shin-Etsu Silicones under the tradename Resin MQ®.

According to another embodiment of this invention, the compositions may contain silsesquioxane resins, including comprise at least one polypropyl silsesquioxane film forming resin.

Silsesquioxane resins are a specific form of silicone resin. Silicone resin nomenclature known in the art as "MDTQ" nomenclature, whereby a silicone resin is described according to the various monomeric siloxane units which make up the polymer. Each letter of "MDTQ" denotes a different type of unit. When the film forming resin is made up predominantly of tri-functional units (or T units), it is generally called a silsesquioxane resin, which is described, for example in US 2006/0292096, herein incorporated by reference.

Examples of silsesquioxane resins that may be used in the present invention are alkyl silsesquioxane resins that are silsesquioxane homopolymers and/or copolymers having an average siloxane unit of the general formula $R^1{}_nSiO_{(4-n)/2}$, wherein each R1 is a propyl group, wherein more than 80 mole % of R1 represent a C3-C10 alkyl group, n is a value of from 1.0 to 1.4, and more than 60 mole % of the copolymer comprises $R^1SiO_{3/2}$ units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference.

A non-limiting example of a polypropylsilsesquioxane resin suitable for se in the present invention is commercially available from Dow Corning as Dow Corning 670 Fluid or Dow Corning 680 Fluid. These Dow Corning resins have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

Another embodiment of this invention, exemplifies the composition containing at least one siloxysilicate resin, at least one silsesquioxane resin and/or mixture thereof.

The at least one silicone resin is generally present in the cosmetic composition of the present invention in an amount ranging from about 5% to about 30% by weight; such as from about 10% to about 25% by weight; such as from about 15% to about 20% by weight, all weights being based on the weight of the composition as a whole.

Polyorganosiloxane Copolymer

The cosmetic compositions of the present invention also comprise at least one polyorganosiloxane-containing polymer. The polyorganosiloxane-containing polymer useful herein is a polymer (homopolymer or copolymer) having at least one moiety which contains: at least one polyorganosiloxane group consisting of 1 to about 1000 organosiloxane units in the chain of the moiety or in the form of a graft, and at least two groups capable of establishing hydrogen interactions. Non-limiting examples of polyorganosiloxane-containing polymers are disclosed, for example in U.S. Pat. No. 8,945,525, the disclosure of which is hereby incorporated by reference.

Additional polyorganosiloxane-containing polymers which may be used in the composition of the invention include those described in documents U.S. Pat. Nos. 5,874,069, 5,919,441, 6,051,216, and 5,981,680, the entire contents of which are hereby incorporated by reference.

A preferred polyorganosiloxane-containing polymer for use in the present invention contain at least one moiety chosen from formula (III):

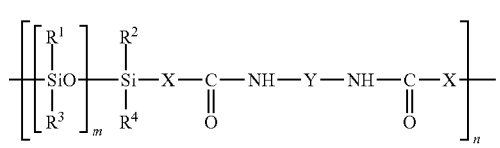

and formula (IV)

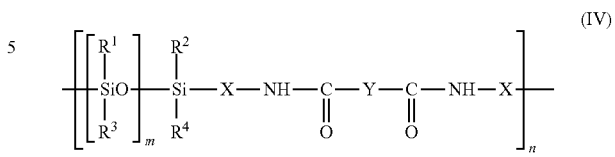

in which:

(a) $R^1$, $R^2$, $R^3$ and $R^4$ are the same or different and may be selected from the group consisting of methyl, ethyl, propyl, isopropyl, a siloxane chain, and phenyl;

(b) X is a linear or branched chain alkylene having 1-30 carbons;

(c) Y is selected from the group consisting of linear or branched chain alkylenes having 1-40 carbons;

(d) m is a number between 1 and 700;

(e) n is a number between 1 and 500.

Particularly preferred polyorganosiloxane-containing polymers useful herein are commercially available from Dow Corning under the tradenames DC 8178® and DC 8179®, which are known under the INCI denomination of Nylon-611/Dimethicone Copolymer.

The at least one polyorganosiloxane-containing polymer is generally present in the cosmetic composition of the present invention in an amount ranging from about 2% to about 35% by weight; such as from about 5% to about 30% by weight; such as from about 7% to about 20% by weight, all weights being based on the weight of the composition as a whole.

Silicone Elastomer (Silicone Crosspolymer)

The composition according to the invention also comprises at least a silicone elastomer.

In a preferred embodiment, the composition comprises a non-emulsifying silicon elastomer.

The non-emulsifying silicon elastomer may be in the form of a gel or a powder.

The "organopolysiloxane elastomer" or "silicon elastomer" or "silicone crosspolymer" thickens the composition, adds the cushiony (spongy) effect and to improves the application of the finished product. Also, it provides a very soft feel and mattifying effect after the application, which is especially advantageous for skin products.

The term "non-emulsifying" defines organopolysiloxane elastomers that do not contain in any hydrophilic chains, and in particular polyoxyalkylene (especially polyoxyethylene or polyoxypropylene) or polyglyceryl units. Thus, according to one particular embodiment of the invention, the composition comprises an organopolysiloxane elastomer that is free of polyoxyalkylene units and polyglyceryl units.

The non-emulsifying elastomers are described in U.S. Pat. No. 8,637,057, the disclosure of which is hereby incorporated by reference.

The non-emulsifying elastomers particularly useful in this invention include but not limit those sold under the names KSG-6, KSG-15, KSG-16, KSG-18, KSG-41, KSG-42, KSG-43 and KSG-44 by the company Shin-Etsu, DC 9040, DC 9041, DC 9509, DC 9505 and DC 9506, by the company Dow Corning, and SFE 839 by the company General Electric.

In an embodiment, the organopolysiloxane elastomer particles are conveyed in the form of a gel formed from an elastomeric organopolysiloxane included in at least one hydrocarbon-based oil and/or one silicone oil. In these gels, the organopolysiloxane particles are often non-spherical particles.

Not limited examples of silicone elastomers useful in this invention are dimethicone crosspolymer gels (blends of dimethicone crosspolymers in solvents) having viscosity values from about 150 and to about 700 mm²/s, from about 200 to about 650 mm²/s and from about 300 to about 600 mm²/s.

Particularly useful for this invention may be blends of high molecular weight silicone elastomers in volatile solvents, such as silicone oils, hydrocarbon oils and mixtures thereof, as per definition disclosed far along.

The specific but not limiting examples of silicone elastomeric gels applicable this invention are represented by DC EL-8040 ID (INCI name: Isododecane (and) Dimethicone Crosspolymer) and DC EL-9140 DM (INCI name: Dimethicone (and) Dimethicone Crosspolymer), supplied by Dow Corning.

Nonlimiting examples of silicone elastomers and their synthesis are disclosed, for example in U.S. Pat. No. 8,637,057 and US/20150174048, all of which are herein incorporated by reference.

This silicon elastomers present in the inventive compositions are generally in a content ranging from 1 percent to 30 percent by weight of active material (dry matter), more preferably from about 1.5 percent to about 20 percent and most preferably from 2 percent to 10 percent by weight relative to the total weight of said composition.

Volatile Solvent

The compositions of the invention contain at least one volatile solvent.

The expression "volatile solvent" means any non-aqueous medium capable of evaporating on contact with the skin or the lips in less than one hour at room temperature and atmospheric pressure.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

The at least one volatile solvent is generally present in the cosmetic composition of the present invention in an amount ranging from about 5% to about 50% by weight; such as from about 10% to about 45% by weight; such as from about 15% to about 40% by weight, all weights being based on the weight of the composition as a whole.

Non-Volatile Solvent

The compositions of the present invention also comprise at least one non-volatile solvent (oil).

The volatility of the oils can be determined using the evaporation speed as set forth in U.S. Pat. No. 6,338,839, the content of which is herein incorporated by reference.

Non-volatile oils include low viscosity oils (having a viscosity from about 5 to about 10 centipoise) and high viscosity oils (having a viscosity of from about 100 to about 10,000 centipoise), and mixtures thereof. In contrast to waxes, oils are liquids at room temperature.

According to a particular embodiment of the present invention, the oil is a high viscosity oil which is a silicone oil and/or a hydrocarbon oil, "High viscosity" means an oil having a viscosity greater than 100 cSt, particularly greater than 250 cSt at 25° C. Most particularly, the non-volatile oil is selected from a silicone oil. Such oils are described, for example in US 2011/0293550 and US 2004/0126350, both of which are herein incorporated by reference.

Non-limiting examples of suitable non-volatile silicone oils include polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes (CTFA designation "dimethicones") comprising alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethione fluids have viscosity from about 350 cPs at 25° C. to about 1000 cPs at 25° C.

Specific examples of suitable for this invention high viscosity silicone oils include, but are not limited to, Xiameter® silicone fluids from Dow Corning.

The at least one non-volatile silicone oil is present in the compositions of the present invention in an amount ranging from about 2% to about 30% by weight, including from about 4% to about 25% by weight, typically about 6% to about 20% by weight, based on the total weight of the composition, including all ranges and subranges within these ranges.

It has been surprisingly discovered that by combining in the inventive composition, at least one silicone elastomer, preferably at least one dimethicone crosspolymer, and at least one non-volatile silicone fluid having a viscosity greater than or equal to 350 cSt at 25° C., in a ratio where the weight of the silicone elastomer to the weight of the non-volatile silicone fluid is higher or equal to from about 1:0.02 and is lower or equals to from about 1:10 by weight (for example, 1:0.02 to 1:10), including all ranges and subranges therebetween such as, for example, from about 1:1 to about 1:6 and from about 1:1 to about 1:5, yield a cosmetic characterized by long wear, transfer resistance, non-tackiness, limited flaking and great comfort.

According to other embodiments, the present invention refers to methods of improving the tackiness, transfer-resistance and/or long wear properties of a composition, comprising incorporating to the composition, at least one silicone elastomer, preferably at least one dimethicone crosspolymer, and at least one non-volatile silicone fluid having a viscosity greater than or equal to 350 cSt at 25° C., in a ratio where the weight of the silicone elastomer to the weight of the non-volatile silicone fluid is higher or equal to from about 1:0.02 and is lower or equals to from about 1:10 by weight (for example, 1:0.02 to 1:10), including all ranges and subranges therebetween such as, for example, from about 1:1 to about 1:6 and from about 1:1 to about 1:5, yield a cosmetic characterized by long wear, transfer resistance, non-tackiness, limited flaking and great comfort.

The compositions of the present invention are useful as compositions for making up the skin, in particular the lips.

Wax (Optional)

The cosmetic compositions of the present invention optionally may contain at least one wax.

For the purposes of the present invention, a wax is a lipophilic fatty compound that is solid at room temperature (25° C.), has a reversible solid/liquid change of state (that is, the state of the material may change based on temperature), has a melting point greater than 45° C., preferably greater than 55° C., more preferably between about 65° C. to about 120° C., and has an anisotropic crystal organization in the solid state. The melting point of the wax may be measured using a differential scanning calorimeter (DSC), for example the calorimeter sold wider the name DSC 30 by Mettler. For waxes that are derived from petroleum, such as microcrystalline wax, the melting point may be measured according to the drop ASTM method, D-127.

The waxes are those generally used in cosmetics and dermatology. The waxes may be of natural origin, for instance beeswax, carnauba wax, candelilla wax, ouricoury wax, Japan wax, cork fiber wax or sugar cane wax, paraffin wax, lignite wax, microcrystalline waxes, lanolin wax, montan wax, ozokerites and hydrogenated oils, for instance hydrogenated jojoba oil.

The waxes also may be of synthetic origin, for instance polyethylene waxes derived from the polymerization of ethylene, waxes obtained by Fischer-Tropsch synthesis, esters of fatty acids and of glycerides that are solid at 40° C.

Waxes of synthetic origin are preferable as they are more uniform and provide greater reproducibility than waxes of natural origin. Moreover, the waxes are preferably not silicone waxes.

Particular waxes include polyethylene waxes, for example the product sold under the name Performalene 500-L Poly-ethylene (New Phase Technology), and polymethylene waxes, for instance the product sold under the name Cirebelle 303 (Sasol).

The cosmetic compositions of the present invention may contain at least one polypropylsilsesquioxane wax substituted with alkyl units having at least 30 carbons.

Polypropylsilsesquioxane waxes, in general, have been disclosed in patent publication WO2005/100444 and U.S. Pat. No. 8,586,013, the entire contents of which are hereby incorporated by reference.

It should be noted, however, that not all polypropylsilsesquioxane waxes yield stable colored cosmetic emulsion products. More particularly, it has been found that only those polypropylsilsesquioxane, waxes substituted with alkyl units having at least 30 carbons are stable.

A particularly preferred polypropylsilsesquioxane wax for use in the present invention is a C30-45 ALKYLDIMETHYLSILYL POLYPROPYLSILSESQUIOXANE commercially available from DOW CORNING under the tradename SW-8005 C30 Resin Wax.

When present in the instant compositions, the at least one wax may be present in an amount ranging from about 0.01% to about 30% by weight, from about 0.02% to about 25%, typically from about 0.03% to 15% by weight, preferably from about 0.05% to about 5% by weight, including all ranges and subranges therebetween, all weights based on the weight of the composition as a whole.

Pigments

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 15%, typically from about 1.5% to about 12%, most typically from about 2% to about 10%, based on the weight of the composition.

Filler

Fillers that may be used in the compositions of the invention include, for example, silica powder; talc; polyimide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc); and mixtures thereof.

The fillers may be present in the composition of the invention in an amount ranging from about 0.1% to about 50% by weight, such as from 0.5% to about 30% by weight, and such as from about 1% to about 20% by weight, all weights based on the weight of the composition as a whole.

As per this invention hydrophobic silica aerogels are particularly useful.

Silica aerogels are porous materials obtained by replacing (by drying) the liquid component of a silica gel with air. They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990. Silica aerogels, in general, have been disclosed in U.S. Pat. No. 9,320,689, the entire content of which is hereby incorporated by reference.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by the company Cabot under the references AEROGEL TLD 201, AEROGEL OGD 201, AEROGEL TLD 203, ENOVA® AEROGEL MT 1100, ENOVA AEROGEL MT 1200.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 $m^2/g$.

The silica aerogel particles can be used in the inventive compositions from 0.1% to about 8% by weight, preferably from 0.25% to 6% by weight, better still from 0.5% to 4% by weight, including all ranges and subranges therebetween, all weights based on the weight of the composition as a whole.

Additives

The compositions of the present invention may further comprise at least one cosmetically or dermatologically acceptable additive such as aa additional thickener, an additional film former, a plasticizer, an antioxidant, an essential oil, a botanical extract, a fragrance, a preserving agent, a fragrance, a pasty fatty substance, a neutralizing agent, and a polymer, and cosmetically active agents and/or dermatological active agents such as, for example, emollients, moisturizers, vitamins, essential fatty acids and medicaments.

As per this inventions, the additives are incorporated from about 0.02% to about 2%, preferably from about 0.1% to about 1.5%, better still from about 0.3% to about 1%.

EXAMPLES

The present invention will be better understood from the examples which follow. The examples are intended to be nonrestrictive and explanatory only, with the scope of the invention defined by the claims.

Method of Preparation of Inventive Composition(s)

The mixture of pigment, isododecane and MQ resin was grinded to create a pigment paste. The blend was processed using Disconti Mill until the paste passed the Hegman Gauge test (ASTM D1210-05). Then, the paste grind was added to the remaining ingredients. The mixture was heated to 80° C. and stirred, until a homogeneous liquid composition was obtained. After that, the inventive composition was cooled down to the room temperature and transferred to desired containers and/or applicators.

Evaluation of Inventive Compositions: Methods and Test Results

The inventive compositions were tested for tackiness and flaking versus control and comparative compositions, Each of the tested products was tested five (5) times. Testing methods are described below.

Tack Testing

The films of each formula were deposited onto contrast cards using a 3 MIL drawdown bar and an Automatic Drawdown Machine. The films were dried at room temperature (25° C.) overnight and analyzed using a Texture Analyzer equipped with a ball probe. Tack force was measured after applying 350 g-force for 10 seconds. Then, the values of the tackiness were correlated to the comfort of wear of the tested products. The samples having the tackiness having values higher than 100 gr/force, were considered to be very uncomfortable to wear. The tack values between 50-100 gr/force, indicated medium comfort, and those with values of less than 50 gr/force were considered to be comfortable.

Flake Testing

Additionally, the samples were tested for flake resistant properties. The samples of all tested compositions were deposited onto the surface of Thera-Band® intermediate resistance exercise band (7×5 cm), using a 3 MIL drawdown bar. The samples were allowed to dry for 4 hours at room temperature (25° C.) and then they were stretched to the length of 30 cm. The stretching was repeated ten (10) times for each of the samples. During the stretching process, flacking of the dry samples was observed and correlated with durability of wear of the tested products. To define the degree of samples' flacking, the following four (4) point grading scale was used: 0—no flaking (very good wear), 1—low flaking (good wear), 2—medium flaking (medium/acceptable wear) and 3—high flaking (no wear).

TABLE 1

Lip Compositions containing DC 8040 silicone elastomer (18% active)

Test results

| Ingredients | Inventive Compositions (% weight) | | | | | | | Control Compositions (% weight) | |
|---|---|---|---|---|---|---|---|---|---|
| | 1 | 2 | 3 | 4 | 5 | 6 | 7 | 1 | 2 |
| MQ | 17.55 | 17.55 | 17.55 | 17.55 | 17.55 | 17.55 | 17.55 | 17.55 | 17.55 |
| PSPA | 9.78 | 9.78 | 9.78 | 9.78 | 9.78 | 9.78 | 9.78 | 9.78 | 9.78 |
| 1000 cst Dimethicone fluid | 12.21 | 12.21 | 12.21 | 6.65 | 6.65 | 9.98 | 9.98 | 0 | 0 |
| Pigment blend | 6.41 | 6.41 | 6.41 | 6.41 | 6.41 | 6.41 | 6.41 | 6.41 | 6.41 |
| Silicone resin wax | 0.5 | 0.5 | 0.5 | 0.5 | 0.5 | 0.5 | 0.5 | 0.5 | 0.5 |
| 8040 Silicone elastomer *(18% active) | 25 (4.5%) | 13.89 (2.5%) | 36.11 (6.5%) | 25 (4.5%) | 13.89 (6.5%) | 25 (4.5%) | 36.11 (6.5%) | 25 (4.5%) | 13.89 (6.5%) |
| Fillers and Lauryl lysine | 4.83 | 4.83 | 4.83 | 4.83 | 4.83 | 4.83 | 4.83 | 4.83 | 4.83 |
| Fragrance | 0.1 | 0.1 | 0.1 | 0.1 | 0.1 | 0.1 | 0.1 | 0.1 | 0.1 |
| Isododecane | QS | QS | QS | QS | QS | QS | QS | QS | QS |
| Ratio of silicone elastomer (% active):dimethicone | 1:2.7 | 1:4.9 | 1:1.9 | 1:1.5 | 1:1.02 | 1:2.2 | 1:1.5 | — | — |
| Tack 1 | 8.5 | 5.3 | 9.8 | 14 | 12.1 | 7.5 | 34.8 | 77.7 | 81.3 |
| Tack 2 | 6.1 | 6.4 | 10.1 | 18.1 | 13.2 | 6.7 | 7.1 | 76 | 69.4 |
| Tack 3 | 7 | 5.5 | 7.4 | 15.9 | 13.3 | 8.6 | 29.5 | 63.7 | 82.9 |
| Tack 4 | 7 | 5.5 | 7.1 | 18 | 11.1 | 7 | 11.5 | 59.4 | 75 |
| Tack 5 | 5.8 | 7 | 8.6 | 19.7 | 16.7 | 9.5 | 37 | 58.8 | 88 |
| Average Tack | 6.9 | 5.9 | 8.6 | 17.1 | 13.3 | 7.9 | 24 | 67.1 | 79.3 |
| Stdev | 1.1 | 0.7 | 1.4 | 2.2 | 2.1 | 1.2 | 13.8 | 9.1 | 7.2 |
| Flaking | 1 | 2 | 1 | 0 | 0 | 0 | 0 | 0 | 0 |

All numerical values in the above table are weight percent active.
*Dow Corning ® EL-8040 ID; INCI Name: Isododecane (and) Dimethicone Inventive compositions of the liquid lip products containing DC 8040 Silicone elastomer and 1000 cSt Dimethicone are represented but not limited by examples in Table 1, as shown below.

It was observed that the inventive compositions having the highest ratio of the silicone elastomer containing 18% of actives to the dimethicone oil was the least tacky indicating a very good comfort and had medium flaking, meaning that the wear was considered to be good. The inventive formulations having lower ratios of the same silicone elastomer to the dimethicone fluid, were characterized by increased tackiness (decreased comfort) and improved flaking (better wear). The tackiness for the control samples without dimethicone oil, was very high meaning that the comfort of wear was very low, and shown no flakiness.

TABLE 2

Lip Compositions containing DC 9140 DM silicone elastomer (14% active)

Test Results

| Ingredients | Inventive Compositions (% weight) | | | | | | Control Composition (% weight) |
|---|---|---|---|---|---|---|---|
| | 8 | 9 | 10 | 11 | 12 | 13 | 3 |
| MQ | 17.55 | 17.55 | 17.55 | 17.55 | 17.55 | 17.55 | 17.55 |
| PSPA | 9.78 | 9.78 | 9.78 | 9.78 | 9.78 | 9.78 | 9.78 |
| 1000 cst Dimethicone fluid | 12.21 | 12.21 | 11 | 10 | 9 | 10 | 0 |
| Lauryl lysine | 1.5 | 1.5 | 1.5 | 1.5 | 1.5 | 1.5 | 1.5 |
| Pigment blend | 6.41 | 6.41 | 6.41 | 6.41 | 6.41 | 6.41 | 6.41 |
| Silicone resin wax | 0.5 | 0.5 | 0.5 | 0.5 | 0.5 | 0.5 | 0.5 |
| 9140 DM Silicone elastomer *(14% active) | 32.14 (4.5%) | 17.86 (2.5%) | 35.71 (5%) | 35.71 (5%) | 35.71 (5%) | 32.14 (4.5%) | 17.86 (2.5%) |
| Fillers | 3.33 | 3.33 | 3.33 | 3.33 | 3.33 | 3.33 | 3.33 |
| Fragrance | 0.1 | 0.1 | 0.1 | 0.1 | 0.1 | 0.1 | 0.1 |

TABLE 2-continued

Lip Compositions containing DC 9140 DM silicone elastomer (14% active)

| | Test Results | | | | | | |
|---|---|---|---|---|---|---|---|
| | Inventive Compositions (% weight) | | | | | | Control Composition (% weight) |
| Ingredients | 8 | 9 | 10 | 11 | 12 | 13 | 3 |
| Isododecane | QS | QS | QS | QS | QS | QS | QS |
| Ratio of silicone elastomer (% active):di-methicone | 1:2.7 | 1:4.9 | 1:2.2 | 1:2 | 1:1.8 | 1:2.2 | — |
| Tack 1 | 6.3 | 6 | 8.9 | 6.3 | 14.7 | 5.6 | 103.6 |
| Tack 2 | 6.8 | 5.5 | 6.8 | 7.4 | 8 | 9.1 | 108.2 |
| Tack 3 | 5.7 | 5.6 | 7.2 | 7 | 10 | 6.9 | 104 |
| Tack 4 | 6 | 6.1 | 7.9 | 7.8 | 11.7 | 7.2 | 89.1 |
| Tack 5 | 8.8 | 5.8 | 8.2 | 8.7 | 9.4 | 10.2 | 74.2 |
| Ave Tack | 6.7 | 5.8 | 7.8 | 7.4 | 10.8 | 7.8 | 95.8 |
| Stdev | 1.2 | 0.3 | 0.8 | 0.9 | 2.6 | 1.8 | 14.1 |
| Flaking | 1 | 0 | 2 | 2 | 2 | 1 | 0 |

All numerical values in the above table are weight percent active.
*Dow Corning ® EL-9140 DM; INCI Name: Dimethicone (and) Dimethicone Crosspolymer Inventive compositions of the liquid lip compositions containing DC 9140 DM Silicone elastomer and 1000 cSt Dimethicone are represented but not limited by examples in Table 2, as shown below.

As per results presented in Table 2, the inventive samples having the highest ratio of the silicone elastomer (containing 14% of actives) to the dimethicone oil was characterized by the lowest tackiness and providing a very good comfort. The samples did not flake, meaning that they demonstrate a very good wear. The inventive formulations having lower ratios of the same silicone elastomer to dimethicone, had increased both, tackiness and flaking. The tackiness for the control sample was very high and had no flaking. That indicates that the absence of dimethicone significantly increased discomfort of wear, although the wear appeared to be improved.

Based on the result presented in the tables above, the absence of dimethicone oil significantly increased the tack. In addition, the decrease of the concentration of actives in silicone elastomer blends and the increase of dimethicone oil having high viscosity, caused the reduction of tackiness. As per the provided examples, the inventive lip liquid compositions having ratios of the silicone elastomer actives to dimethicone oil from about 1:0.05 to about 1:5 were considered to be very comfortable to wear with minimal or no flaking (good wear).

TABLE 3

Relation between viscosities of dimethicone oils and tackiness and flacking of lip liquid compositions

| Ingredients/ Test Results | Composition w/1000 cst dimethicone oil | Composition w/350 cst dimethicone oil | Composition w/100 cst dimethicone oil | Composition without dimethicone oil |
|---|---|---|---|---|
| MQ | 17.55 | 17.55 | 17.55 | 17.55 |
| PSPA | 9.78 | 9.78 | 9.78 | 9.78 |
| 1000 cst Dimethicone fluid | 12.21 | 0 | 0 | 0 |
| 350 cst Dimethicone fluid | 0 | 12.21 | 0 | 0 |
| 100 cst Dimethicone fluid | 0 | 0 | 12.21 | 0 |
| Caprylyl methicone | 0 | 0 | 0 | 12.21 |
| Lauryl lysine | 1.5 | 1.5 | 1.5 | 1.5 |
| Pigment blend | 6.41 | 6.41 | 6.41 | 6.41 |
| Silicone resin wax | 0.5 | 0.5 | 0.5 | 0.5 |
| 9140 DM Silicone elastomer* (14% active) | 17.86 | 17.86 | 17.86 | 17.86 |
| Fillers | 3.33 | 3.33 | 3.33 | 3.33 |
| Fragrance | 0.1 | 0.1 | 0.1 | 0.1 |
| Isododecane | QS | QS | QS | QS |
| Tack 1 | 6.0 | 5.1 | 64.0 | 35.3 |
| Tack 2 | 5.5 | 4.6 | 56.4 | 34.7 |
| Tack 3 | 5.6 | 4.8 | 61.8 | 34.9 |
| Tack 4 | 6.1 | 5.2 | 49.5 | 36.2 |
| Tack 5 | 5.8 | 4.6 | 41.2 | 36.8 |
| Ave tack | 5.8 | 4.9 | 54.6 | 35.6 |
| Stdev | 0.3 | 0.3 | 9.3 | 0.9 |
| Flaking | 1 | 0 | 0 | 0 |

All numerical values in the above table are weight percent active.
*Dow Corning ® EL-9140 DM; INCI Name: Dimethicone (and) Dimethicone Crosspolymer In order to determine the most suitable dimethicone fluid for this invention, three (3) dimethicone oils having different viscosity (at 25° C.) were tested for tackiness and flacking: 1000 cSt at, 350 cSt and 100 cSt.

Based on the results in Table 3, the composition which contained dimethcione oil having viscosity of 100 cSt, was the most tacky. It was followed by the composition which did not contain the dimethicone oil at all (including Comparative 3 from table 2), and formulation containing 1000 cSt dimethicone, and 350 cSt dimethicone respectively. All tested formulations were characterized by no flaking or minimal flaking.

TABLE 4

Evaluation of tackiness and flacking of commercial lip compositions

| Test Results | Comparator A | Comparator B | Comparator C |
|---|---|---|---|
| Tack1 | 80.9 | 11.1 | 119.1 |
| Tack2 | 84.4 | 8.2 | 135.0 |
| Tack 3 | 118.6 | 4.2 | 150.1 |
| Tack 4 | 123.1 | 7.4 | 129.3 |
| Tack 5 | 104.5 | 8.5 | 146.5 |
| Average Tack | 102.3 | 7.9 | 136.0 |
| Standard deviation | 19.2 | 2.5 | 12.7 |
| Flaking | 0 | 1 | 1 |

In order to define improvement of the inventive lip liquid compositions, three (3) commercially available long wear and transfer resistant lip products were studied for the flacking and tackiness. The compositions of the tested comparators are shown below, as well as the results of the tests.

Comparator A: (1 step color coat liquid lipstick): isododecane, trimethylsiloxysilicate, nylon-611/dimethicone copolymer, disteardimonium hectorite, lauroyl lysine, c30-45 alkyldimethylsilyl polypropylsilsesquioxane, alumina, propylene carbonate, synthetic fluorphlogopite, silica, calcium sodium borosilicate, calcium aluminum borosilicate, polyethylene terephthalate, parfum/fragrance, aluminum hydroxide, acrylates copolymer, benzyl alcohol, dimethicone, paraffin, tin oxide. [+/– may contain/peut contenir mica, ci 77891/titanium dioxide, ci 77491, ci 77492, ci 77499/iron oxides, ci 15850/red 7, ci 15985/yellow 6 lake, ci 45410/red 28 lake, ci 45380/red 22 lake, ci 19140/yellow 5 lake, ci 42090/blue 1 lake, ci 75470/carmine] f.i.l. d41008/5

Comparator B:

Base coat (2 step lip liquid products: color coat and liquid top coat): isododecane, trimethylsiloxysilicate, nylon-611/dimethicone copolymer, disteardimonium hectorite, lauroyl lysine, c30-45 alkyldimethylsilyl polypropylsilsesquioxane, alumina, propylene carbonate, synthetic fluorphlogopite, silica, calcium sodium borosilicate, calcium aluminum borosilicate, polyethylene terephthalate, parfum/fragrance, aluminum hydroxide, acrylates copolymer, benzyl alcohol, dimethicone, paraffin, tin oxide. [+/– may contain/peut contenir mica, ci 77891/titanium dioxide, ci 77491, ci 77492, ci 77499/iron oxides, ci 15850/red 7, ci 15985/yellow 6 lake, ci 45410/red 28 lake, ci 45380/red 22 lake, ci 19140/yellow 5 lake, ci 42090/blue 1 lake, ci 75470/carmine] f.i.l. d41008/5

Top coat (liquid): trimethyl pentaphenyl trisiloxane, isdiglyceryl polyacyladipate-2, ozokerite, cera alba/beeswax/cire dabeille, calcium sodium borosilicate, calcium aluminum borosilicate, tocopheryl acetate, parfum/fragrance. [+/– may contain/peut contenir mica, ci 77891/titanium dioxide, ci 77491/iron oxides]

Comparator C: (1 step liquid color coat lipstick): isododecane, Dimethicone, Trimethylsiloxysilicate, Polyethylene, Synthetic Fluorphlogopite, Disteardimonium Hectorite, C12-15 Alkyl Benzoate, Propylene Carbonate, Silica, Calcium Sodium Borosilicate, Methicone, Sorbic Acid. May Contain: Mica, Titanium Dioxide (Ci 77891), Iron Oxides (Ci 77491, 77492, 77499), Red 7 Lake (Ci 15850), Red 6 Lake (Ci 15850), Yellow 5 Lake (Ci 19140), Red 33 Lake (Ci 17200), Yellow 6 (Ci 15985), Carmine (Ci 75470).

As per results presented above, commercially available long-wear, transfer resistant products did not provide a good comfort as indicated by very high tack values (over 100 gr/force). According to the data, Product C (1 step liquid lipstick) had the tackiness values above 100 gram/force, it was followed by product A (also 1 step liquid lipstick). However, the tackiness of Product B (2 step product involving color coat and top coat) was very low and comparable with tackiness of the inventive compositions (Table 1, examples 1-7).

What is claimed is:

1. A liquid cosmetic composition comprising:
   (a) from about 2% to about 10% by weight of at least one silicone elastomer relative to a total weight of the composition;
   (b) from about 6 to about 20% by weight of at least one dimethicone fluid having a viscosity greater than 300 cSt and lower than 1200 cSt at 25° C.;
   (c) from about 2% to about 35% by weight of at least one Nylon-611/Dimethicone copolymer relative to the total weight of the composition;
   (d) from about 5% to about 30% by weight of at least one silicone resin relative to the total weight of the composition, wherein the at least one silicone resin is selected from the group consisting of siloxysilicate resins, silsesquioxane resins, and mixture thereof;
   (e) from about 5% or about 50% by weight of at least one volatile solvent relative to the total weight of the composition; and
   (f) from 0% to about 5% by weight of wax relative to the total weight of the composition;
   wherein a weight ratio of the silicone elastomer (a) to the at least one dimethicone fluid (b) is from 1:1 to 1:5,
   the weights being relative to a total weight of the composition,
   the composition provides a matte appearance to lips after application, and
   the composition is substantially free of non-volatile phenylated solvents.

2. The composition of claim 1, wherein the at least one silicone elastomer is at least one non-emulsifying silicone elastomer.

3. The composition of claim 1 wherein the at least one silicone elastomer is at least one dimethicone crosspolymer in an amount from about 2% to about 10% by weight relative to the total weight of the composition.

4. The composition of claim 1 wherein the at least one Nylon-611/Dimethicone copolymer is present in the composition in an amount from about 7% to about 20% by weight, relative to the total weight of the composition.

5. The composition of claim 1 wherein the at least one silicone resin is trimethylsiloxysilicate.

6. The composition of claim 5, wherein the at least one silicone resin is present in the composition in an amount from about 10% to about 20% by weight, relative to the total weight of the composition.

7. The composition of claim 1 wherein the at least one volatile solvent is present in the composition in an amount from about 15% to about 40% by weight, relative to the total weight of the composition, and the volatile solvent is selected from the group consisting of hydrocarbon oils, silicone oils, and mixtures thereof.

8. The composition of claim 1, further comprising at least one colorant present in the composition in an amount from about 0.5% to about 15% by weight, relative to the total weight of the composition.

9. The composition of claim 1, comprising wax present in the composition in an amount from about 0.05% to about 5% by weight, relative to the total weight of the composition.

10. The composition of claim 1, further comprising at least one filler present in the composition in an amount from about 0.1% to about 50% by weight, relative to the total weight of the composition.

11. The composition according to claim 9, wherein polypropylsilsesquioxane wax substituted with alkyl units having at least 30 carbon atoms is present in the composition.

12. The composition according to claim 1, wherein the silicone elastomer is present in the composition in an amount less than the amount of the at least one dimethicone fluid present in the composition, and wherein the composition exhibits improved properties with respect to tackiness, comfort, and flaking as compared to compositions comprising less silicone elastomer (a) than at least one dimethicone fluid (b).

13. The composition according to claim 1, wherein the composition is free of non-volatile phenylated solvents.

14. A liquid lipstick having the composition of claim 1.

* * * * *